(12) United States Patent
DeHart

(10) Patent No.: US 8,177,730 B2
(45) Date of Patent: May 15, 2012

(54) BLOOD EXPRESSION DEVICE

(75) Inventor: Damon DeHart, Bedford, MA (US)

(73) Assignee: Abbott Laboratories, Abbot Park, IL (US)

( * ) Notice: Subject to any disclaimer, the term of this patent is extended or adjusted under 35 U.S.C. 154(b) by 0 days.

(21) Appl. No.: 12/485,292

(22) Filed: Jun. 16, 2009

(65) Prior Publication Data

US 2009/0312669 A1 Dec. 17, 2009

Related U.S. Application Data

(62) Division of application No. 10/974,477, filed on Oct. 27, 2004, now Pat. No. 7,775,990.

(51) Int. Cl.
*A61B 5/00* (2006.01)
*B65D 81/00* (2006.01)

(52) U.S. Cl. ........................................ 600/583; 600/573

(58) Field of Classification Search ................. 600/583, 600/584, 573; 606/181–183
See application file for complete search history.

(56) References Cited

U.S. PATENT DOCUMENTS

| | | | | |
|---|---|---|---|---|
| 5,392,778 A | * | 2/1995 | Horzewski | 600/434 |
| 6,319,210 B1 | * | 11/2001 | Douglas et al. | 600/583 |
| 6,752,817 B2 | * | 6/2004 | Flora et al. | 606/181 |
| 7,201,723 B2 | * | 4/2007 | Chan | 600/583 |
| 2002/0010406 A1 | * | 1/2002 | Douglas et al. | 600/583 |
| 2002/0022789 A1 | | 2/2002 | Perez et al. | |
| 2005/0215925 A1 | * | 9/2005 | Chan | 600/583 |
| 2006/0184189 A1 | * | 8/2006 | Olson et al. | 606/181 |

FOREIGN PATENT DOCUMENTS

| | | |
|---|---|---|
| WO | 2004/045375 A2 | 6/2004 |
| WO | 2005/034778 A1 | 4/2005 |
| WO | 2005/094684 A1 | 10/2005 |

* cited by examiner

*Primary Examiner* — Max Hindenburg
*Assistant Examiner* — H. Q. Nguyen
(74) *Attorney, Agent, or Firm* — Young Basile

(57) ABSTRACT

An embodiment of a device for expressing blood from a wound site formed in dermal tissue is constructed in the shape of a cap removably mounted onto a lancing instrument. The blood expression device includes an annular support member and a plurality of movable fingers integrally formed onto the support member in a spaced apart relationship, the free ends of the plurality of fingers together defining a generally circular opening. Each finger is adapted for pivotal displacement in such a manner that its free end projects into the circular opening. In use, the free ends of the plurality of fingers are disposed in contact against the dermal tissue immediately surrounding the wound site. As the device is urged downward onto the dermal tissue, the free ends of the plurality of fingers collapse inward from the force of an axially movable sleeve and pinch into the dermal tissue, resulting in the expression of blood.

6 Claims, 7 Drawing Sheets

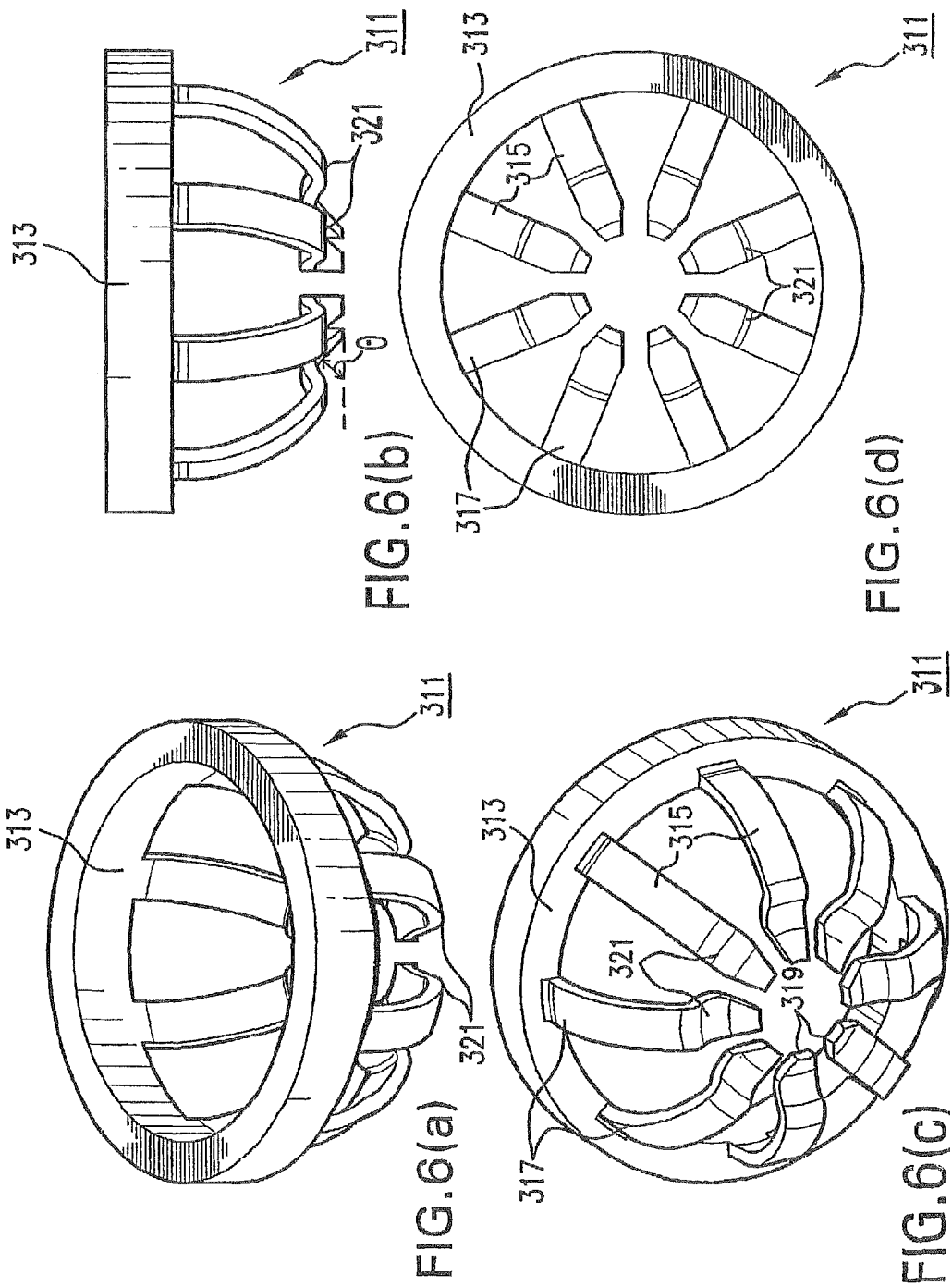

BLOOD EXPRESSION DEVICE

CROSS REFERENCE TO RELATED APPLICATION

This application is a divisional application of and claims priority from U.S. patent application Ser. No. 10/974,477, filed on Oct. 27, 2004, which is incorporated herein in its entirety by reference.

FIELD OF THE INVENTION

The present invention relates in general to lancing instruments and relates more particularly to a blood expression device for use with a lancing instrument.

BACKGROUND

There are many medical conditions for which it is desirable to draw a blood sample from a patient for analysis. For example, in the case of certain communicable diseases, a blood sample drawn from a patient may be analyzed for the presence of a blood borne pathogen. Alternatively, in the case of diabetes, blood samples drawn periodically from a patient may be used to monitor blood sugar levels.

Blood samples taken from a patient for blood sugar monitoring are typically obtained by piercing the skin of the patient using a lancing instrument (also referred to herein as a lancing device). A lancing instrument typically includes a body and a lancet. The body is typically adapted to be held by the user, the lancet being coupled to the body and being adapted to penetrate through the epidermis (the outermost layer of the skin) of the patient and into the dermis (the layer of skin directly beneath the epidermis) which is replete with capillary beds. The puncture of one or more capillaries by the lancet generates a sample of blood which exits through the incision in the patient's skin.

In some lancing devices, the lancet is fixedly coupled to the body. In other lancing devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with such force that contact of the moving lancet tip with the skin of a patient results in the piercing of the skin of the patient. In many such lancet devices having a movable lancet, the lancet is automatically drawn back into the body after reaching its extended position (e.g., using a spring) in order to minimize the risk of inadvertent lancet sticks.

Lancing instruments of the type described above are commonly used to lance dermal tissue. However, it has been found that, in certain situations, blood does not readily emanate from the wound site in the lanced skin. Rather, after puncturing the skin, conventional lancing devices are typically laid down onto a flat surface and, in a subsequent step, the user pinches, squeezes and/or kneads the dermal tissue surrounding the wound site in order to express out an adequate blood sample which can then be collected and analyzed for testing purposes.

As can be appreciated, it has been found that the aforementioned process for collecting a blood sample has a number of significant shortcomings.

As a first shortcoming, the aforementioned process is rather complex and requires a considerable level of manual dexterity. Specifically, the fact that the user is required to lay down the lancing instrument in between the lancing and blood expression processes, renders the aforementioned process somewhat difficult for many people (e.g., elderly patients) to perform, which is highly undesirable.

As a second shortcoming, the aforementioned process may introduce contaminants onto the lancing instrument. Specifically, in those situations where a lancing instrument is to be used for multiple lancing operations, the user must ensure that the lancing instrument is placed on a clean storage site after the lancing procedure but before commencing the blood expression process. If the lancing instrument is not placed on a sterile surface, the user subjects him/her self to potentially harmful contaminants when performing future lancing operations using the same lancing instrument, which is highly undesirable.

BRIEF SUMMARY

It is an object of the present invention to provide a novel device for expressing blood from a wound site formed in dermal tissue.

It is another object of the present invention to provide a blood expression device as described above which has a limited number of parts, which is inexpensive to manufacture and which is easy to use.

Therefore, according to one feature of the present invention, there is provided a device for expressing blood from a wound site in dermal tissue, the device comprising, a support member, and a plurality of movable fingers coupled to the support member.

As another feature of the present invention, there is provided a device for expressing blood from a wound site in dermal tissue, the device comprising, a crimping member, the crimping member comprising, a support member, and a plurality of movable fingers coupled to the support member, and a sleeve slidably mounted over the crimping member, the sleeve being sized and shaped to selectively exert an inward force onto each movable finger.

As another feature of the present invention, there is provided a method of generating a blood sample from dermal tissue, the method comprising the steps of lancing the dermal tissue so as to create a wound site, and after the lancing step, expressing blood out from the wound site using a blood expression device which comprises a support member, a plurality of movable fingers coupled to the support member, and a sleeve configured to exert an inward force on the fingers.

As another feature of the present invention, there is provided the combination of a lancing instrument, the lancing instrument including a sharpened needle, and a blood expression device, mounted on the lancing instrument over the sharpened needle, the blood expression device comprising a support member and a plurality of movable fingers coupled to the support member.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

The description herein makes reference to the accompanying drawings wherein like reference numerals refer to like parts throughout the several views, and wherein:

FIGS. 6(a)-(d) are top perspective, front plan, bottom perspective and bottom plan views of a fourth embodiment of a blood expression device which is constructed according to the teachings of the present invention.

DETAILED DESCRIPTION OF EMBODIMENTS OF THE INVENTION

Figure 1A:
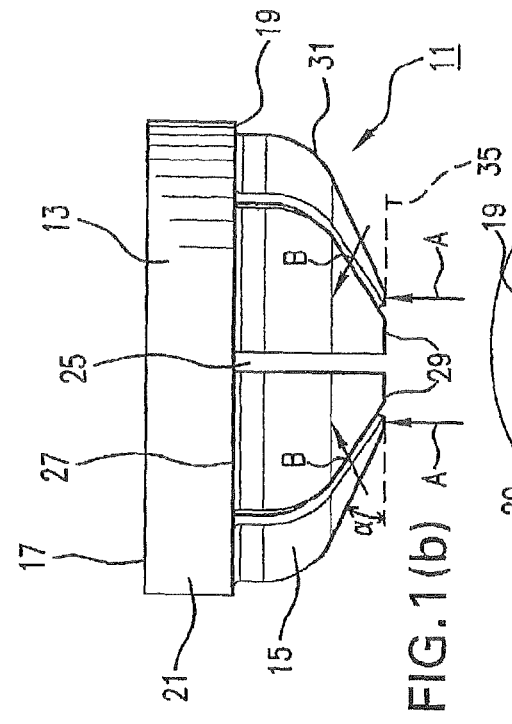
FIGS. 1(a)-(d) are top perspective, front plan, bottom perspective and bottom plan views, respectively, of a first embodiment of a blood expression device which is constructed according to the teachings of the present invention.

Referring now to the drawings, there is shown in FIGS. 1(a)-(d) a first embodiment of a blood expression device that is constructed according to the teachings of the present invention and identified generally by reference numeral 11. As will be described further in detail below, device 11 is designed to facilitate the expression of blood from a wound site formed in dermal tissue.

Blood expression device 11 is a unitary member which is preferably constructed out of a rigid and resilient plastic material using conventional molding techniques. Blood expression device 11 is represented herein as being in the form of a removable cap for a conventional lancing instrument (as will be discussed further below) and includes a support member 13 and a plurality of movable fingers 15.

Support member 13 is constructed as an annular band, or ring, which includes a substantially flat top surface 17, a substantially flat bottom surface 19, a curved outer surface 21 and a curved inner surface 23. Preferably, support member 13 is designed to facilitate the connection of device 11 to the distal end of a conventional lancing instrument, as will be described further below. For example, support member 15 may be sized and shaped to be telescopingly mounted over the distal end of the lancing instrument in a press-fit interrelationship. As another example, threading (not shown) may be provided on curved inner surface 23 to allow for device 11 to be screwed over the distal end of a complementary lancing instrument (which is similarly provided with threading on its outer surface).

Fingers 15 are integrally formed onto bottom surface 19 of support member 13, each finger 15 being configured to extend downward and inward relative to bottom surface 19. Fingers 15 are preferably spaced equidistantly apart from one another, adjacent fingers 15 being separated by a narrow slot 25, thereby allowing for the independent articulation (i.e., flexion) of each finger 15.

It should be noted that device 11 is represented herein as comprising eight separate movable fingers 15. However, it is to be understood that device 11 is not limited to a particular number of movable fingers 15. Rather, it is to be understood that device 11 could be constructed with a greater number (e.g., 10) or fewer number (e.g., 6) of movable fingers 15 without departing from the spirit of the present invention.

Each finger 15 has a thin, slightly curved, wedged-shaped configuration. Specifically, each finger 15 includes a first end 27 which is integrally formed onto bottom surface of support member 13 and a free second end 29, the lateral cross-section of finger 15 tapering gradually inward from its first end 27 to its second end 29. As such, first end 27 has a substantial width whereas second end 29 has a relatively narrow width (e.g., approximately 3.0 mm).

As noted briefly above, each finger 15 is contoured with a vertical component as well as a radial component. Specifically, each finger 15 initially extends downward from bottom surface 19 at an approximate right angle relative thereto (i.e., the vertical component). At its approximate midpoint, each finger 15 is provided with a bend 31 which, in turn, orientates second end 29 at a downward and inward (i.e., the radial component) angle relative to support member 13.

Figure 1B:
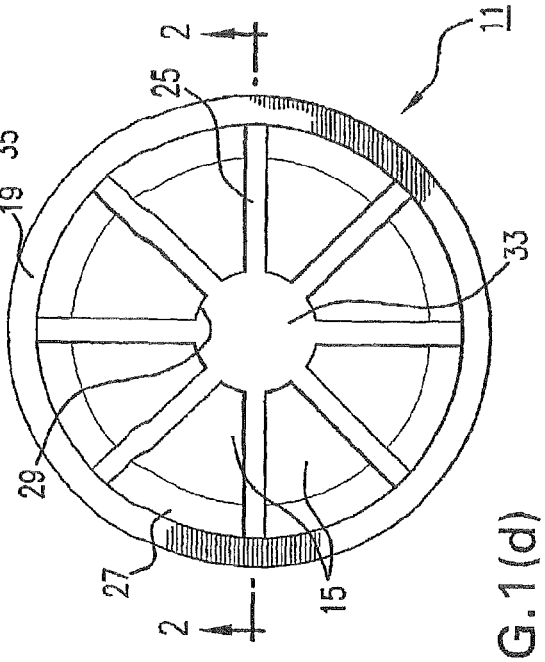
Figure 1C:
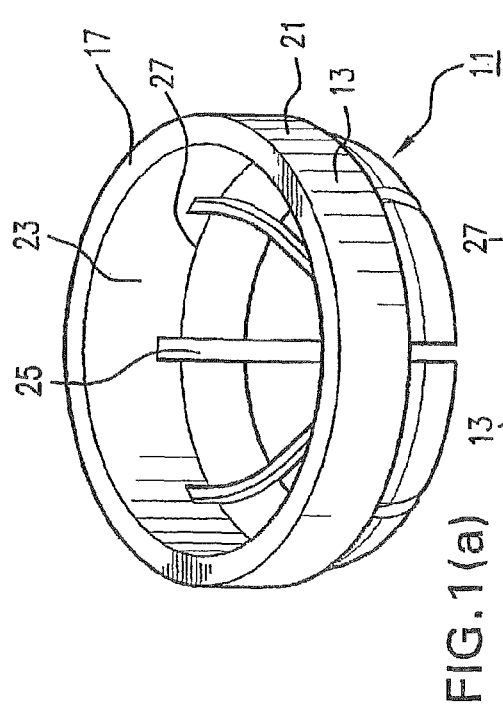
Figure 1D:
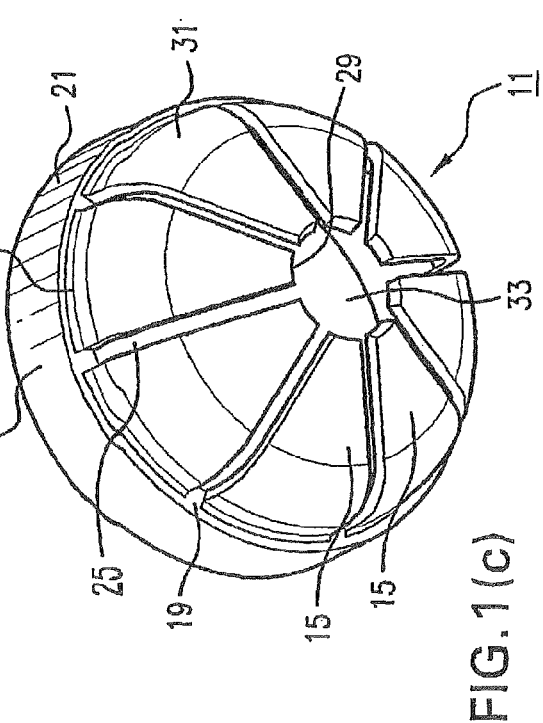

Second ends 29 of fingers 15 at least partially define a generally circular opening 33, as seen most clearly in FIGS. 1(c) and 1(d). As will be described further in detail below, a wound site formed in dermal tissue is preferably centered within circular opening 33 during the blood expression process. In this manner, free second ends 29 of fingers 15 can be used to apply a circumferential ring of pressure around the wound site-which, in turn, serves to promote blood expression, which is highly desirable.

Second ends 29 of fingers 15 together define a common planar contact surface, said planar surface being shown in dashed form in FIG. 1(b) and identified generally by reference numeral 35. Due to the co-planar configuration of second ends 29, fingers 15 are all disposed to contact the dermal tissue which immediately surrounds the wound site with equal force. In this manner, the circumferential ring of pressure created around the wound site during the blood expression process is uniform in force, which is highly desirable.

It should be noted that the free second end 29 of each finger 15 terminates at an acute angle α of approximately 25 degrees relative to co-planar surface 35, as seen most clearly in FIG. 1(b). As can be appreciated, the particular pitch of angle α can be increased or decreased in order to modify the degree of the blood extraction force which is applied circumferentially around the wound site by device 11 (wherein an increase in angle α serves to increase the degree of the blood extraction force and a decrease in angle α serves to decrease the degree of the blood extraction force).

As can be appreciated, the particular shape of each finger 15 allows for its flexion about bend 31 such that free second end 29 is capable of pivoting upward and inward. Specifically, the application of a vertical force (as represented by arrows A in FIG. 1(b)) onto the free second end 29 of each finger 15 causes second end 29 to pivot upward and inward (as represented by arrows B in FIG. 1(b). Due to its manufacture out of a resilient material, the withdrawal of said vertical force causes fingers 15 to return to their original orientation.

The flexion of second ends 29 about their associated bends 31 serves to inwardly draw (i.e., collapse) fingers 15 towards one another which, in turn, serves to reduce, or constrict, the size (i.e., the lateral cross-sectional area) of opening 33. Specifically, in the absence of a vertical force onto the free second end 29 of fingers 15, the diameter of opening 33 is approximately 10 mm. However, upon the application of a vertical force onto the free second end 29 of fingers 15 which is roughly 1.0-3.0 pounds, the diameter of opening 33 constricts to approximately 7.0-8.0 mm. It is this inward flexibility of fingers 15 that is used to express blood from a wound site in dermal tissue, as will be described further in detail below.

Specifically, referring now to PIGS. 2(a)-(b) device 11 can be used in the following manner to express blood from a wound site in dermal tissue. With a wound site W having been formed in dermal tissue D (e.g., using a lancing instrument), a small blood sample S often collects within wound site W beneath the surface of dermal tissue D, as seen most clearly in FIG. 2(a). In this situation, the user is required to apply a force onto the dermal tissue D which immediately surrounds the wound site W in order to express out an adequate supply of blood B for testing purposes.

Accordingly, with wound site W having been formed in dermal tissue D, blood expression device 11 is disposed against the dermal tissue which immediately surrounds wound site W. In particular, device 11 is positioned such that second end 29 of fingers 15 are all drawn in contact against dermal tissue D, with wound site W centered within opening 33. As such, second end 29 of fingers 15 form a circumferential ring around wound site W.

Figure 2A:
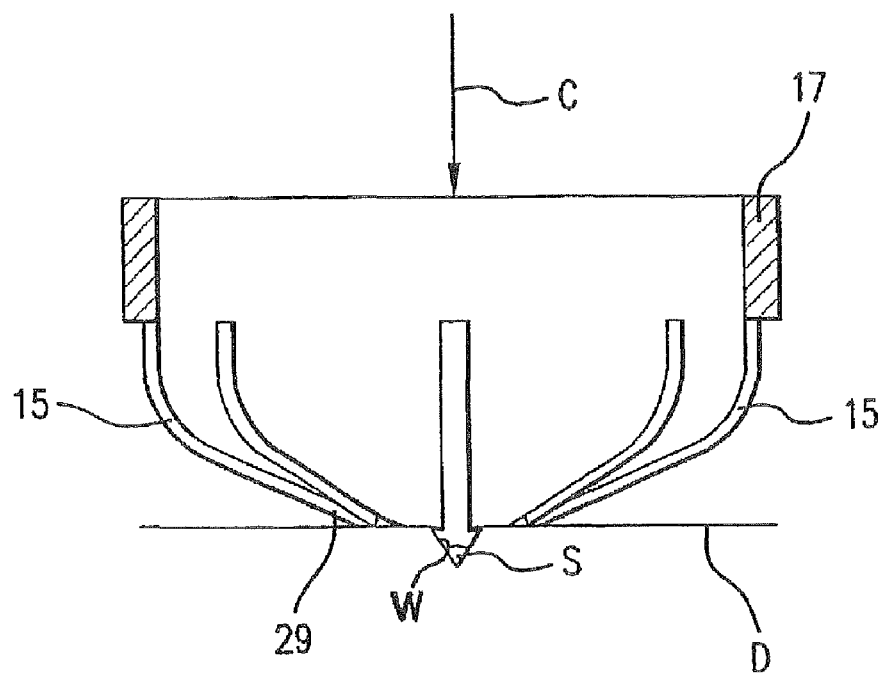
FIGS. 2(a)-(b) are section views of the blood expression device shown in FIG. 1(d), taken along lines 2-2, at various stages during the process of expressing blood from a wound site formed in dermal tissue.
Figure 2B:
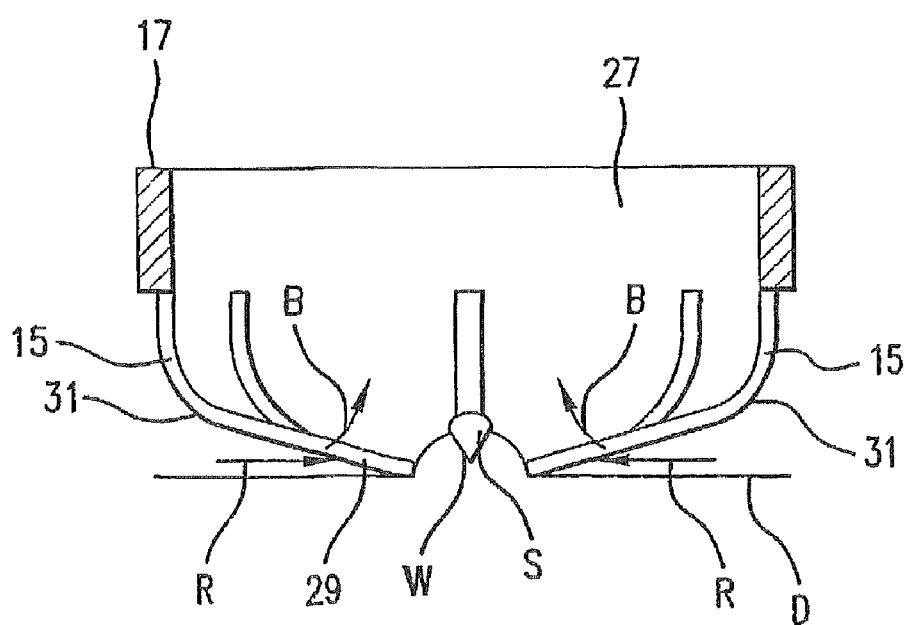

Having positioned device 11 as such, a downward force is applied onto top surface 17, the downward force being represented by arrow C in FIG. 2(a). The application of this downward force, in turn, causes the dermal tissue D to flex, or pivot, each finger 15 upward and inward about its associated bend 31, as represented by arrows B in FIG. 2(b). As fingers 15 flex, second ends 29 collapse in towards one another, thereby decreasing the cross-sectional area of opening 33. In turn, the second end 29 of each finger 15 applies an inward radial force (as represented by arrows R in FIG. 2(b)) onto the dermal tissue D which immediately surrounds the wound site W. As a result, second ends 29 actively pinch (i.e., crimp) the dermal tissue D immediately surrounding the wound site W and pull said tissue upward until the dermal tissue D immediately surrounding the wound site W bulges, or distends, above the common planar contact surface 35 which is defined by the second ends 29 of the various fingers 15. With the dermal tissue D distended in this manner, blood sample S naturally expresses from the wound site W, which is the principal object of the present invention.

As noted briefly above, device 11 is represented herein as being in the form of a cap which can be removably mounted onto the distal end of a conventional lancing instrument. In this manner, the lancing instrument can be used to generate a wound site in the test area and, without removing the lancing instrument from the test area, the blood expression device 11 can be urged down against test area with suitable pressure so that an adequate blood sample is expressed from the wound site, as will be described further in detail below.

Figure 3:
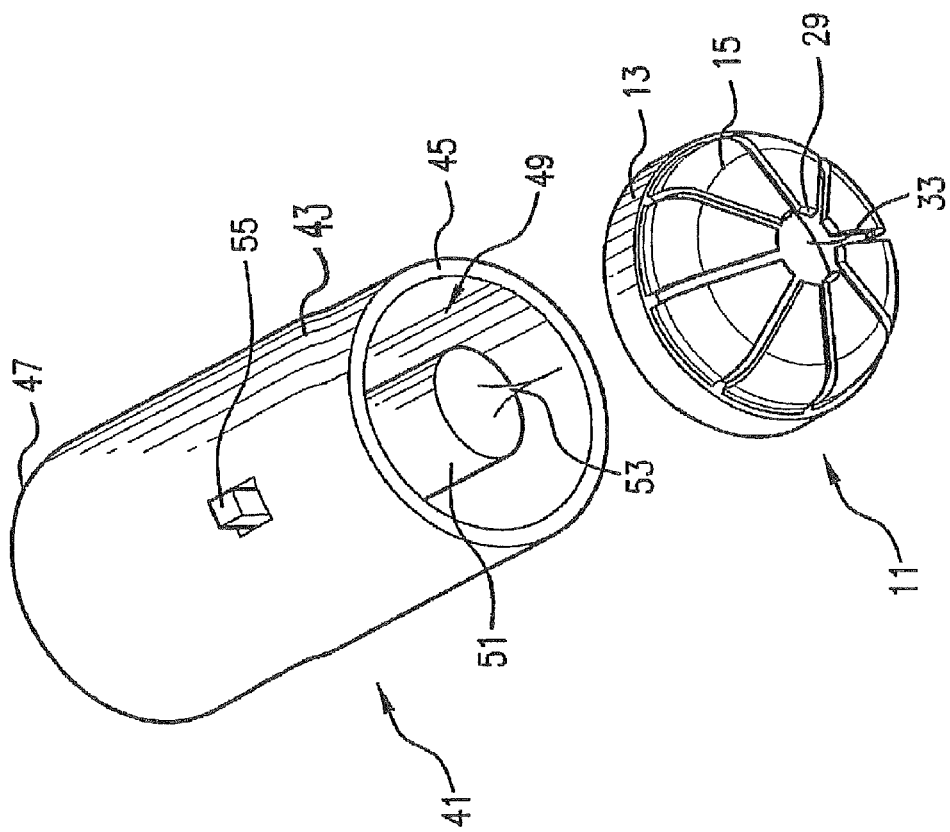
FIG. 3 is a front perspective view of the blood expression device shown in FIG. 1(c), the blood expression device being shown exploded away from a compatible lancing instrument.

Specifically, referring now to FIG. 3, there is shown a lancing instrument 41 with which blood expression device 11 may be used. As will be described further below, blood expression device 11 is sized and shaped to be removably mounted onto lancing instrument 41 so as to create a single apparatus which can be used to both lance dermal tissue as well as express blood from the lanced dermal tissue.

Lancing instrument 41 (also referred to herein as a lancing device) includes a housing 43 which is represented herein as having a pen-shaped, tubular design. Housing 43 includes a distal end 45, a proximal end 47 and is at least partially hollowed out so as to define an interior chamber 49.

A movable lancet 51 is coupled to housing 43 by means of, inter alia, a spring (not shown) and is adapted for longitudinal displacement within interior chamber 49. Lancet 51 is provided with a sharpened needle 53 which is adapted for penetration into capillary beds present within dermal tissue.

Cocking means (not shown) is provided for manually storing energy in the spring. It should be noted that the storage of energy into the cocking means is usually accompanied by the retraction of moveable lancet 51 within housing 43 towards proximal end 47 (i.e., such that sharpened needle 53 does not extend past distal end 45 of housing 43).

Trigger means 55 is additionally provided for releasing energy stored in the spring, trigger means 55 being represented herein as being in the form of a manually depressible button. The release of energy stored in the spring is used to drive lancet 51 forward (i.e., in the direction towards distal end 45). It should be noted that the release of energy stored in the spring is of such force so as to enable sharpened needle 53 to penetrate into dermal tissue.

In use, lancing instrument 41 and blood expression device 11 can be used in combination to extract a blood sample from dermal tissue in the following manner. Specifically, device 11 is secured onto distal end 45 of housing 43. With device 11 mounted onto lancing instrument 41, the cocking mechanism for lancing instrument 41 is then activated which, in turn, stores energy within the spring-biased movable lancet 51. It should be noted that, with the cocking mechanism activated, the tip of sharpened needle 53 is disposed adequately behind second end 29 of fingers 15.

The user, in one hand, positions second end 29 of fingers 15 against the dermal tissue of the desired test site (e.g., a fingertip on the opposite hand which is handling instrument 41). It should be noted that instrument 41 is preferably handled such that fingers 15 exert limited pressure onto the dermal tissue (i.e., with such force that fingers 15 do not collapse).

With lancing instrument 41 and device 11 positioned as such, the firing mechanism for lancing instrument 41 is activated (e.g., through the depression of button 55) which, in turn, expels movable lancet 51 longitudinally through interior chamber 49 in the direction towards distal end 45. The firing of movable lancet 51 causes sharpened needle 53 to pass through opening 33 and penetrate into the dermal tissue which, in turn, creates a wound site in the dermal tissue which is located at the approximate midpoint between each of the second ends 29 of fingers 15.

Having lanced the skin in the manner as described above, device 11 is then used to express a blood sample from the wound site. Specifically, without removing second ends 29 of fingers 15 from the surface of the dermal tissue, instrument 41 urged forcefully towards the skin. As instrument 41 is forced down against the skin, fingers 15 collapse onto the dermal tissue to form a uniform ring of pressure circumferentially around the wound site. The ring of pressure created by fingers 15 causes the dermal tissue immediately surrounding the wound site to significantly bulge which, in turn, causes blood to express out from the wound, as is desired.

Lancing instrument 41 (as well as device 11 which is mounted thereon) is removed from the dermal tissue to allow for the collection of the blood sample (e.g., for testing purposes). Device 11 can then be removed from lancing instrument 41 or retained thereon for future blood drawings.

It should be noted that the fact that mounting device 11 is mounted directly onto lancing instrument 41 serves to effectively combine both the lancing and blood expression processes into a single process. As a result, the user is provided with a simple means of acquiring a blood sample, which is the principal object of the present invention.

As noted above, blood expression device 11 is not limited to use with lancing device 41. Rather, it is to be understood that device 11 could be used with alternative types of lancing instruments which are well known in the art without departing from the spirit of the present invention. For example, it should be noted that the cocking and/or trigger means for lancing instrument 41 could be replaced with electromechanical systems (e.g., solenoids, voice coils, etc.) without departing from the spirit of the present invention. In addition, it is to be understood that device 11 could be used individually (i.e., without any complementary lancing instrument) to express blood from a wound site without departing from the spirit of the present invention.

It should be noted that the particular design of device 11 renders it optimal for blood expression from the fingertip of a patient (i.e., with dermal tissue which is softer and more replete with capillary beds). However, it is has been found that a patient's fingertip includes a substantial number of nerve endings and, as a consequence, is relatively sensitive to pain.

Accordingly, alternate site blood testing is well known in the art and is commonly utilized to reduce patient discomfort when acquiring a blood sample. For example, the forearm of a patient has been found to be a less sensitive test site than a fingertip. However, it is typically more difficult to express blood from alternate test sites due to the smaller concentration of capillary beds found therein as well as the harder (i.e., less meaty) nature of the test site. As a result, a greater blood expression force is often required in order to draw the blood from an alternate test site (i.e., a greater blood expression force than is capable using device 11).

Figures 4B, 4D:
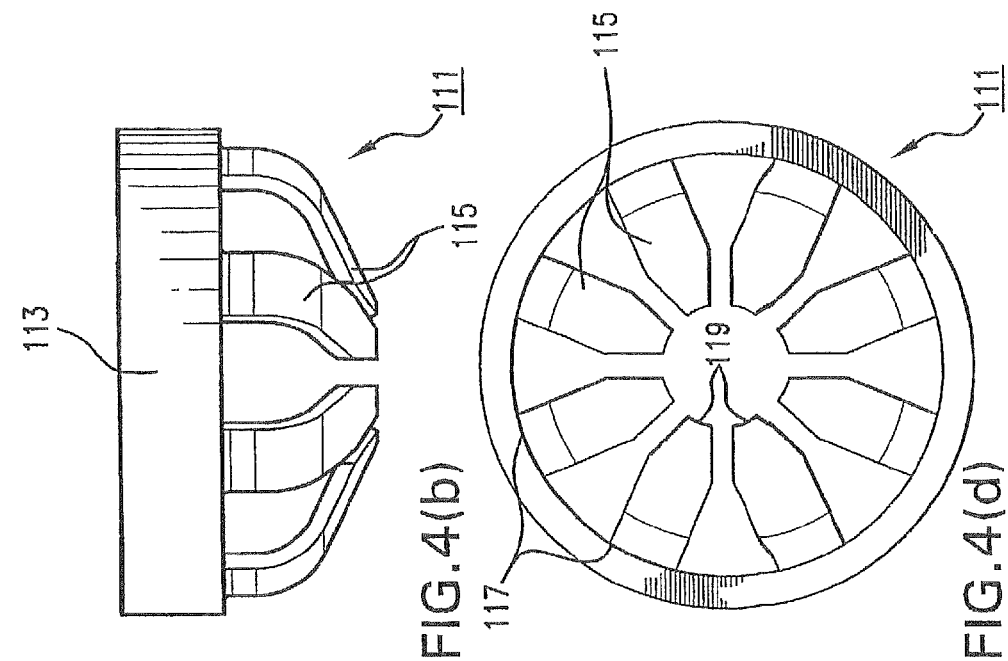
FIGS. 4(a)-(d) are top perspective, front plan, bottom perspective and bottom plan views of a second embodiment of a blood expression device which is constructed according to the teachings of the present invention.
Figures 4A, 4C:
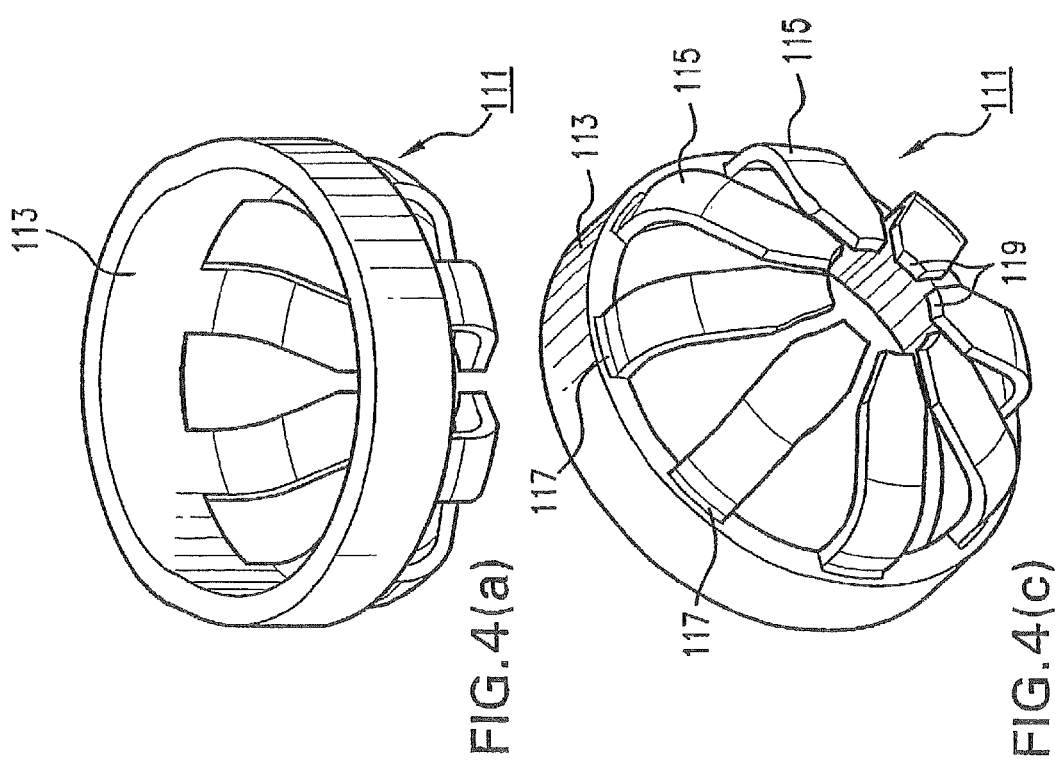
Figure 5B:
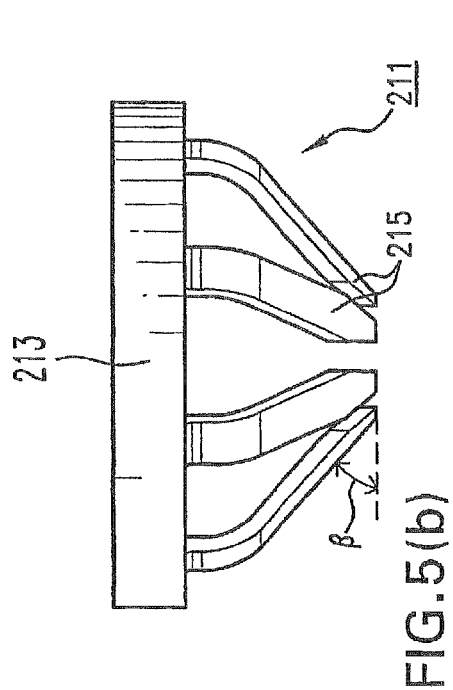
FIGS. 5(a)-(d) are top perspective, front plan, bottom perspective and bottom plan views of a third embodiment of a blood expression device which is constructed according to the teachings of the present invention.
Figure 5D:
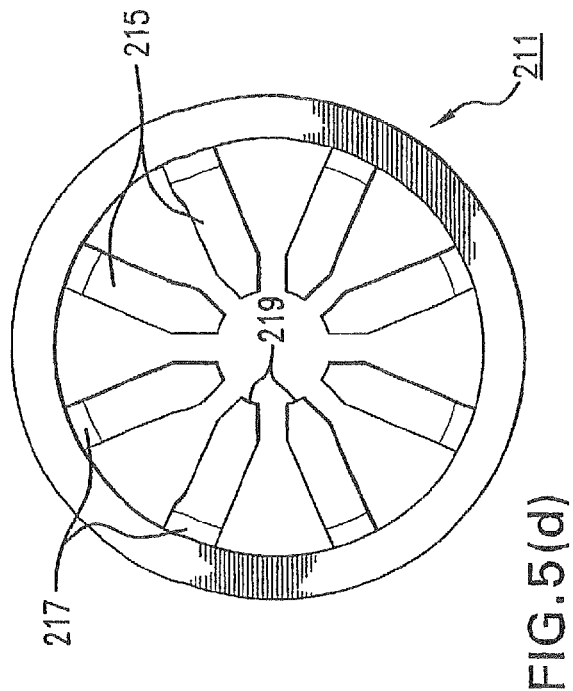
Figure 5A:
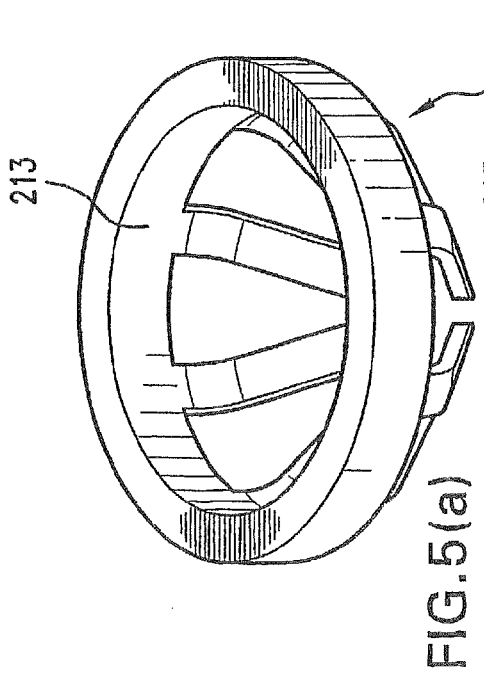
Figure 5C:
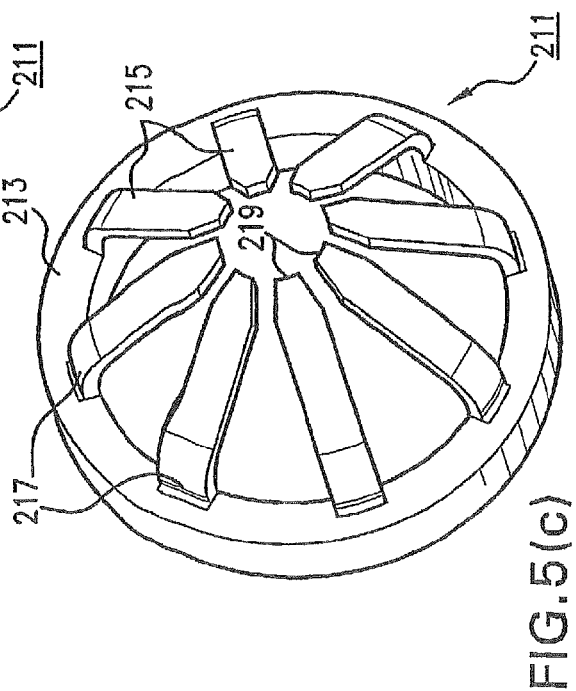

In order to generate a greater blood expression force (i.e., for alternate site testing), device 11 may be modified in accordance with the teachings of the present invention. Specifically, referring now to FIGS. 4(*a*)-(*d*), there is shown a second embodiment of a blood expression device that is constructed according to the teachings of the present invention and identified generally by reference numeral 111. As will be discussed further below, the primary distinction between device 111 and device 11 is that device 111 is capable of providing a greater blood extraction force on dermal tissue than device 11 (and, as a consequence, is more desirable for use in alternate site testing).

Device 111 is similar to device 11 in that device 111 is an integral piece which includes a support member 113 and a plurality of movable fingers 115.

However, there is one principal distinction between device 111 and device 11. Specifically, device 111 differs from device 11 in that each movable finger 115 in device 111 has a different shape in lateral cross-section than each movable finger 15 in device 11. As seen most clearly in FIGS. 4(*c*) and 4(*d*), each finger 115 is of a considerably narrow design and includes a first end 117 and a second end 119. Each finger 115 is substantially uniform in width along the majority of its length, said width being equal to the width of finger 115 at first end 117. Each finger 115 then sharply tapers inward at second end 19 to create a sharper (i.e., more narrow) tip that is more useful in biting, or pinching, into the dermal tissue to promote greater blood expression. Because each finger 115 has a reduced width, it is to be understood that the spacing between adjacent fingers 115 is greater than between adjacent fingers 15 in device 11.

It is to be understood that the significantly more narrow design of fingers 115 (and in particular the sharper tip at second end 119) affords device 111 with the ability to apply a greater blood extraction force (i.e., the pinching or crimping force) onto the dermal tissue than device 11. Stated another way, fingers 115 pinch, or crimp, the dermal tissue surrounding the wound site with a greater force than fingers 15 and, therefore, are more suitable for extracting blood from an alternate, low blood volume test site (e.g., a forearm).

Referring now to FIGS. 5(*a*)-5(*d*), there is shown a third embodiment of a blood expression device that is constructed according to the teachings of the present invention and identified generally by reference numeral 211. As will be discussed further below, the primary distinction between device 211 and device 111 is that device 211 is capable of providing a greater blood extraction force on dermal tissue than device 111.

Device 211 is similar to device 111 in that device 211 is an integral piece which includes a support member 213 and a plurality of movable fingers 215. However, there are two principal distinctions between device 211 and device 111.

As a first distinction, device 211 includes fingers 215 which have a different shape in lateral cross-section than fingers 115 in device 111. Specifically, each finger 215 is of a slightly more narrow design than fingers 115, each finger 215 including a first end 217 and a second end 219. Due to its narrow construction, it is to be understood that each finger 215 terminates at second end 219 so as to create a sharper (i.e., more narrow) tip than finger 115. As a result, each finger 215 is more useful in biting, or pinching, into dermal tissue to promote greater blood expression.

As a second distinction, device 211 includes fingers 215 which have a different contour, or bend angle, than fingers 115 in device 111. Specifically, each finger 215 terminates at a steeper angle $\beta$ (e.g., approximately 50 degrees relative to the co-planar surface defined by second ends 219 of fingers 215) than fingers 115 in device 111. As a result of the steeper angle of fingers 215, device 211 is more useful in biting, or pinching, into dermal tissue to promote greater blood expression.

Referring now to FIGS. 6(*a*)-6(*d*), there is shown a fourth embodiment of a blood expression device that is constructed according to the teachings of the present invention and identified generally by reference numeral 311. As will be discussed further below, the primary distinction between device 311 and device 211 is that device 311 is capable of providing a greater blood extraction force on dermal tissue than device 211.

Device 311 is similar to device 211 in that device 311 is an integral piece which includes a support member 313 and a plurality of movable fingers 315. However, there is one principal distinction between device 311 and device 211.

Specifically, device 311 includes fingers 315 which have a different contour than fingers 215 in device 211. Specifically, each finger 315 is provided with a more curved contour than fingers 211 in device 211, each finger 315 including a first end 317 and a second end 319. As seen most clearly in FIGS. 6(*b*) and 6(*c*), each finger 315 gradually curves inward and downward from first end 317, curves sharply upward and inward so as to form a concave bump 321 between first and second ends 317 and 319, and then terminates downward and inward at a steep angle $\theta$ at its second end 319 (approximately 45 degrees relative to the co-planar surface defined by second ends 319 of fingers 315). As can be seen most clearly in FIG. 6(*d*), all of the bumps 321 together at least partially define an outer ring which is concentric with the inner ring that is at least partially defined by second ends 319. It is to be understood that both the inner ring (i.e., second ends 319) and the outer ring (i.e., bumps 321) apply pressure on the dermal tissue during a blood extraction process which uses device 311. As can be appreciated, it has been found that these two separate rings of concentric pressure applied to the dermal tissue around the wound site increase the amount of blood expressed by device 311 when compared to device 211, which includes only a single ring of pressure.

Figure 7:
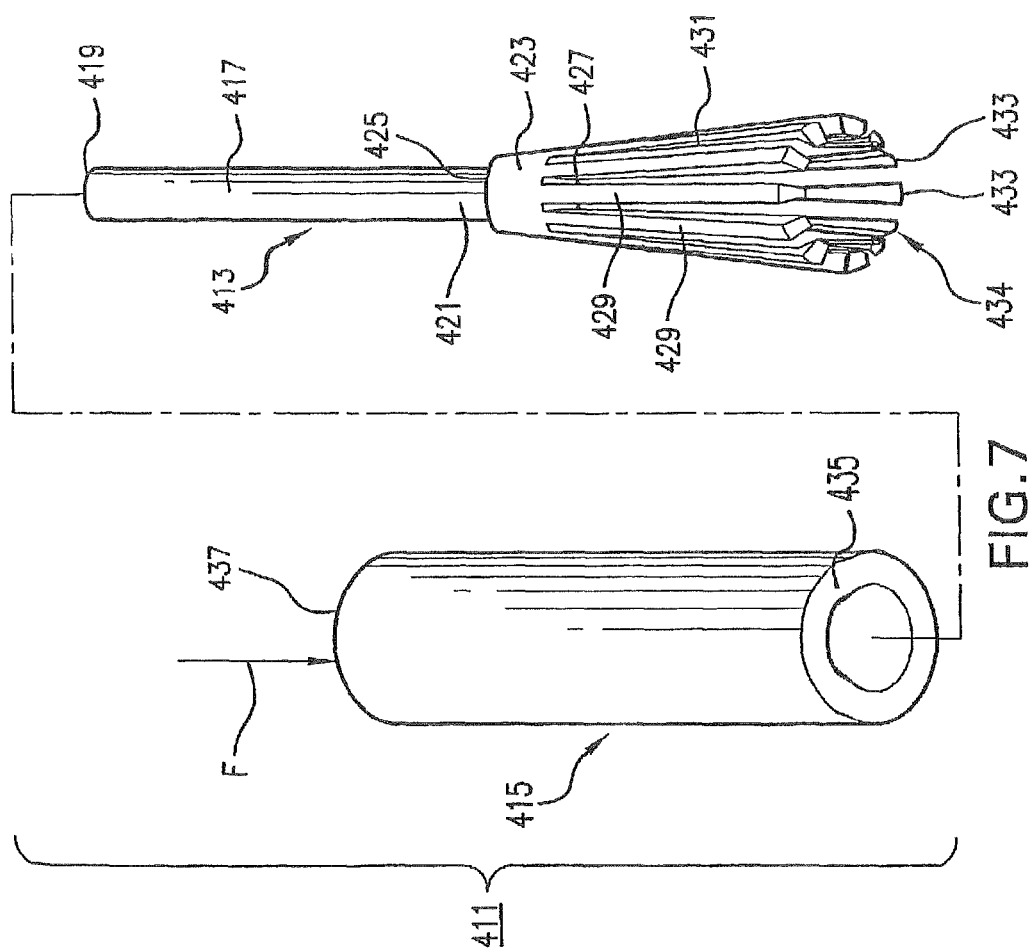
FIG. 7 is an exploded bottom perspective view of a fifth embodiment of a blood expression device constructed according to the teachings of the present invention.

Referring now to FIG. 7, there is shown a fifth embodiment of a blood expression device that is constructed according to the teachings of the present invention and identified generally by reference numeral 411. As will be discussed further below, device 411 can be used in a similar manner as device 11 to extract blood from a wound site formed in dermal tissue.

Device 411 differs from device 11 in that device 411 comprises two separate components, namely a crimping member 413 and a tubular sleeve 415.

Crimping member 413 includes an elongated post 417. Post 417 is generally cylindrical in shape and includes a first end 419 and second end 421. A support member 423 is formed onto second end 421 of post 417. Support member 423 is in the form of an annular band, or ring, which includes a substantially flat top surface 425 and a substantially flat bottom surface 427.

A plurality of fingers 429 are integrally formed onto bottom surface 427 of support member 423. Each finger 429 extends down from bottom surface 427 and is biased slightly outward (i.e., away from the other fingers 429). Fingers 429 are spaced equidistantly apart from one another, adjacent fingers 429 being separated by a narrow slot 431 which thereby allows for the independent articulation of each finger 429.

The free end of each finger 429 is formed into a relatively sharp tip 433, device 411 being naturally biased such that adjacent tips 433 are spaced slightly apart from one another in the absence of any outside force. Tips 433 of fingers 429 are co-planar and together define a generally circular opening 434 therebetween.

Tubular sleeve 415 is represented herein as being in the form of a hollow cylinder which includes an open first end 435 and an open second end 437. Tubular sleeve 415 is sized and shaped to slide axially over crimping member 413. Specifically, post 417 is preferably inserted into tubular sleeve 415 through open end 435 such that sleeve 415 contacts and frictionally slides over the outer surface of fingers 429.

With sleeve 415 slidably mounted over crimping member 413 as such, device 411 can be used in the following manner to express blood from a wound site. Specifically, with a wound site having been formed in the dermal tissue, blood expression device 11 is urged vertically down against the dermal tissue which surrounds the wound site, with the wound site centered between tips 433. As such, tips 433 form a circumferential ring around the wound site. Having positioned device 411 as such, tubular sleeve 415 is slid downward along crimping member 413 in the direction represented by arrow F in FIG. 7.

It should be noted that, as sleeve 415 slides down along crimping member 413, sleeve 415 urges tips 433 radially inward. The displacement of tips 433 radially inward causes tips 433 to actively pinch the dermal tissue immediately surrounding the wound site, thereby causing said tissue to bulge substantially. With the dermal tissue distended in this manner, blood exits the wound site, as is desired.

After an adequate blood sample has been expressed from the wound site, sleeve 415 is slid away from fingers 429 which, in turn, causes fingers 429 to resiliency articulate away from one another and back to their original position. As a result, fingers 429 withdraw from crimping the skin and, as a result, device 411 can be removed from the dermal tissue.

It should be noted that device 411 allows for the separation of the vertical and radial components of force that is applied onto the skin during the blood expression process. Specifically, the vertical component of force is applied by manually urging crimping member 413 down onto the skin surface. The radial component, however, is applied solely through the downward translation of sleeve 415 over crimping member 413. As a result, the user is afforded the opportunity to independently regulate the vertical and radial crimping forces that are applied onto the skin, which is of particular significance in certain applications.

The embodiments shown in the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of generating a blood sample from dermal tissue, the method comprising the steps of:
   (a) lancing the dermal tissue so as to create a wound site, and
   (b) after the lancing step, expressing blood out from the wound site with a blood expression device having a crimping member and a sleeve, the step of expressing blood comprised of:
      placing proximate the wound site the crimping member having a longitudinal axis, and a support member with a first end and a second end and a plurality of movable fingers coupled to the first end of the support member, each movable finger extending from the support member at an outward bias away from the longitudinal axis;
      slidably placing an open end of the sleeve over the second end of the support member, wherein the sleeve is configured to move inward each movable finger; and
      moving the sleeve along the longitudinal axis over the movable fingers toward the dermal tissue, wherein as the sleeve moves toward the wound site, an amount of inward movement of each movable finger increases, wherein the inward movement of each movable finger expresses the blood from the wound site.

2. The method of claim 1 wherein the step of expressing blood further comprises forcing in a vertical direction on the dermal tissue the plurality of movable fingers while forcing in a radial direction on the dermal tissue the plurality of movable fingers with the sleeve.

3. The method of claim 1 wherein each movable finger includes a first end affixed to the support member and a free second end and wherein the sleeve selectively exerts a force onto each movable finger which causes its free second end to pivot inward.

4. The method of claim 1 further comprising the step of:
   (c) selectively removing the inward force on each movable finger after an adequate blood sample has been expressed by moving the sleeve along the longitudinal axis away from the dermal tissue to expose the movable fingers.

5. The method of claim 1 wherein each movable finger is configured to extend down from the support member and bias radially outward and wherein the step of moving the sleeve comprises gradually overcoming the bias to move the fingers gradually radially inward.

6. The method of claim 5 further comprising the step of:
   (c) sliding the sleeve off of the plurality of movable fingers by moving the sleeve along the longitudinal axis away from the dermal tissue such that the plurality of movable fingers resiliently return to an outwardly biased position after an adequate blood sample has been expressed.

* * * * *